United States Patent
Tomulewicz

(10) Patent No.: US 11,058,738 B2
(45) Date of Patent: *Jul. 13, 2021

(54) HERBAL PREPARATION FOR ACCELERATING WOUNDS AND SKIN INFLAMMATIONS HEALING, ESPECIALLY FOR TREATMENT OF HERPES AND ACNE, AND ITS APPLICATION

(71) Applicant: WYŻSZA SZKOŁA MEDYCZNA W BIAŁYMSTOKU, Bialystok (PL)

(72) Inventor: Mikołaj Tomulewicz, Białystok (PL)

(73) Assignee: WYZSZA SZKOLA MEDYCZNA W BIALYMSTOKU, Bialystok (PL)

( * ) Notice: Subject to any disclaimer, the term of this patent is extended or adjusted under 35 U.S.C. 154(b) by 156 days.

This patent is subject to a terminal disclaimer.

(21) Appl. No.: 16/284,802

(22) Filed: Feb. 25, 2019

(65) Prior Publication Data

US 2019/0183954 A1 Jun. 20, 2019

Related U.S. Application Data

(63) Continuation-in-part of application No. 16/035,601, filed on Jul. 14, 2018, now Pat. No. 10,213,469, which is a continuation-in-part of application No. 15/201,619, filed on Jul. 5, 2016, now abandoned.

(30) Foreign Application Priority Data

Jul. 9, 2015 (PL) .................................... P.413074
Oct. 2, 2015 (EP) .................................... 15460092

(51) Int. Cl.
| | | |
|---|---|---|
| A61K 36/00 | (2006.01) | |
| A61K 36/53 | (2006.01) | |
| A61K 47/10 | (2017.01) | |
| A61K 47/44 | (2017.01) | |
| A61P 31/22 | (2006.01) | |
| A61K 31/045 | (2006.01) | |
| A61K 31/131 | (2006.01) | |
| A61K 47/38 | (2006.01) | |
| A61P 17/02 | (2006.01) | |
| A61K 9/00 | (2006.01) | |

(52) U.S. Cl.
CPC ............ *A61K 36/53* (2013.01); *A61K 9/0014* (2013.01); *A61K 31/045* (2013.01); *A61K 31/131* (2013.01); *A61K 47/10* (2013.01); *A61K 47/38* (2013.01); *A61K 47/44* (2013.01); *A61P 17/02* (2018.01); *A61P 31/22* (2018.01)

(58) Field of Classification Search
None
See application file for complete search history.

(56) References Cited

U.S. PATENT DOCUMENTS 5,061,491 A 10/1991 Deryabin

FOREIGN PATENT DOCUMENTS

| CH | 671336 A5 | 8/1989 |
|---|---|---|
| ES | 2080697 B1 | 9/1996 |
| KR | 101464914 B1 | 11/2014 |
| PL | 104273 A1 | 10/1979 |
| RU | 2027440 C1 | 1/1995 |
| RU | 2031645 C1 | 3/1995 |
| RU | 2373950 C1 | 11/2009 |
| RU | 2450836 C1 * | 5/2012 |

OTHER PUBLICATIONS

Grujic et al, Evaluation of antioxidant activity of *Melittis melissophyllum* L. extracts. Archives of Biological Sciences (2014), vol. 66, No. 4, pp. 1401-1410. (Year: 2014).*
International Search Report for corresponding International Patent Application No. PCT/GE 97/00001, dated Nov. 14, 1997.

* cited by examiner

*Primary Examiner* — Qiuwen Mi
(74) *Attorney, Agent, or Firm* — Myers Wolin, LLC

(57) ABSTRACT

An object of the application is a herbal preparation which can be applied in a wound and skin inflammation healing, especially in treatment of herpes and acne, wherein the herbal preparation is characterized in that the preparation contents of emulsified or suspended in an organic medium extract of *Melittis melissophyllum* L. from 10% to 40% w/w and ethyl alcohol from 10% to 20% w/w, wherein in case of an ointment as an organic medium was used vaseline album from 40% to 70% w/w, in case of a gel—glycerol or propylene glycol 2% w/w, triethylamine 2% w/w, hydroxycellulose 1% w/w and purified water, *aqua purificata*, from 30% to 35% w/w.

11 Claims, No Drawings

HERBAL PREPARATION FOR ACCELERATING WOUNDS AND SKIN INFLAMMATIONS HEALING, ESPECIALLY FOR TREATMENT OF HERPES AND ACNE, AND ITS APPLICATION

CROSS-REFERENCE TO RELATED APPLICATIONS

This a non-provisional application, being filed under section 35 U.S.C. 111(a), is a continuation-in-part application of the application Ser. No. 16/035,601, filed Jul. 14, 2018, (matured into a U.S. Pat. No. 10,213,469 to be issued on Feb. 26, 2019) which is a continuation-in-part of the application Ser. No. 15/201,619, filed Jul. 5, 2016, that claims benefits of the Polish Patent Application No. P.413074, filed on Jul. 9, 2015, and of the European Patent Application No. EP15460092, filed on Oct. 2, 2015, pursuant to section 35 U.S.C. 119, and provisions of the Paris Convention Treaty, contents of which are incorporated herein by reference.

A subject matter of the present application is a herbal preparation with anti-inflammatory and astringent effects used in a herbal medicine to treat conditions related to interruption of anatomical continuity of outer layers of skin or deeper tissues, especially herpes and acne.

DESCRIPTION OF RELATED ART INCLUDING INFORMATION DISCLOSED UNDER 37 CFR 1.97 AND 37 CFR 1.98

Herbal preparations are widely used in herbal medicine, cosmetology, and conventional medicine. They have special properties due to presence of biologically active substances that act on skin after their application.

Surface skin inflammations constitute a very serious skin care problem. When untreated or inadequately treated the surface skin inflammations can cause an infection. A healing process is painful and often limits mobility and decreases quality of life of a patient.

All significant injuries lead to damage of vessels and interruption of their anatomical continuity thereby initiating a molecular and cellular response leading to hemostasis, a process that causes bleeding to stop by keeping blood within a damaged blood vessel. This is the first stage of a wound healing.

The healing process cannot be initiated until hemostasis mechanisms start to work, what is a multifactorial and a multistep process. The most important element of hemostasis is blood clotting, leading to clot formation. A blood clot consists mainly of a mesh of fibrin and embedded on it platelets. The clot formation is a very important process. It prevents further loss of fluids and electrolytes from a wound and reduces pollutions coming from outside environment.

The healing process of skin can be accelerated by actions of all kind of chemical substances mainly of synthetic origin which often give rise to additional side effects mainly weakening elasticity of the skin what destructively affects contained in it proteins.

A current treatment of the above-referenced disorders generally involves use of an ointment with steroids and in cases of disorders with chronic conditions, with presence of a variety of bacteria, use of strong antibiotics which often cause adverse side effects.

Another way of treating skin injuries is use of calendula ointment, which contains calendula and Vaseline. When such ointment is used, however, the healing process is slower, and microorganisms can easily be reproduced on a crust formed on wound surface.

In a treatment of a skin inflammation, including wounds, also special herbal compositions with a synergistic effect are used.

U.S. Ser. No. 10/034,908 (B2) discloses a herbal composition for the treatment of skin diseases, especially herpes and shingles. An individual suffering from a viral disease of the skin is administered topically to the skin in a therapeutically effective amount, either aqueous or aqueous-alcoholic, or a natural extract of vegetable oil from a dandelion. As a natural vegetable oil, linseed oil or other oil available, e.g. almond oil, coconut oil, jojoba oil, lemon oil, olive oil, sesame seed oil and sunflower oil, etc., can be used. This patent teaches that aqueous and aqueous-alcoholic extracts of green dandelions, leaves and roots can be used for the local treatment of herpes simplex virus type 1 (HSV-1) and herpes zoster (VZV).

The Russian patent RU2373950 (C1) teaches a composition for the prevention and/or treatment of diseases associated with colds caused by influenza virus and herpes simplex, which contains as active ingredients a common antiviral agent selected from the group: tetraxolin, bonaphton, tetrabrometretrahydroxydiphenyl and extract from the medical plant selected from the group of plants: licorice, coneflower, aloe, garlic, cat's claw, calendula, chamomile, linden, birch buds, tea tree in a certain ratio.

From the published international application no. WO2010076812 is known a herbal nanoemulsion formulation comprising a combination of lemon juice and/or rose water as a therapeutically active aqueous phase trapped in an oil phase selected from one or more essential oils that can also be used for topical acne and other treatments, skin disorders such as eczema, psoriasis, etc.

A patent number KR101464914 (B1) teaches a composition comprising natural healing herbal extracts and natural sulfur as the main active ingredients for improving skin function, regenerating skin cells and treating acne at the same time without side effects for the human body. The composition contains an herbal extract obtained by mixing *Scutellaria baicalensis, Phellodendron amurense, Gardenia jasminoides* and *Portulaca oleracea, Sophora flavescens* extract, *Coptis chinensis* extract, *Poria cocas* extract and natural organic sulfur.

There is a trend in world medicine of seeking natural substances that may replace synthetic ones in a treatment of skin injuries.

An object of the present application is an application of medical preparations, based on a herbal extract for a treatment of conditions associated with interruption of anatomical continuity of outer layers of skin or deeper tissues, which leads to an accelerated healing process and obtaining desired results even in the treatment of chronic and inflammatory complications after a surgery. This and other objects and advantages of the herbal preparation will become apparent from a detailed description which follows.

BRIEF DESCRIPTION

It was established, based on experiments, that the herbal preparation according to the present application has comparable bactericidal and bacteriostatic properties with pharmacological formulations. The herbal preparation has an exacerbated therapeutic effect leading to rapid self-cleaning of a skin inflammation with interruption of the anatomical continuity of the outer layers or the deeper tissues and leading to their complete healing without causing side effects.

The herbal preparation, for herpes and acne treatment, according to the present application, contains a plant extract emulsified or suspended in an organic based medium, characterized in that it contains, as an active substance, an alcoholic extract from *Melittis melissophyllum* L, and other active substances such as flavonoids in the amount of from 3.6% to 13.4% by weight, polyphenols in the amount of from 11.25% to 45% by weight, tannins in the amount of from 5% to 8% by weight, amine compounds in the amount of from 0.475% to 1.9% by weight, bitter substances in the amount of from 11.55% to 46.2% by weight, and mineral salts in the amount of from 6% to 10% by weight.

The alcoholic extract of *melittis* contains a *Melittis melissophyllum* L. herb in the amount from 10% to 40% w/w, and ethyl alcohol in the amount from 10% to 20% w/w.

The herbal preparation in the form of an ointment contains, as an organic basis, Vaseline album in the amount from 40% to 70% w/w.

According to an aspect of one preferred embodiment of the herbal preparation, in the form of an ointment or gel, contains as an organic basis glycerol or propylene glycol in the amount of 2% w/w, trimethylamine in the amount of 2% w/w, hydroxycellulose in the amount of 1% w/w, and purified water (*aqua purificata*) in the amount from 30% to 35% w/w.

Another aspect of the herbal preparation is use of the herbal preparation to treat various types of wounds and skin inflammations.

The herbal preparation, according to the present patent application, causes normal growth of epithelium and accelerates granulation of skin tissues. It helps to maintain, for a longer period of time, moisture of wound environment what accelerates a wound filling, where due to a long lapse of time destruction of connective and subcutaneous tissue occurred, and accelerates a growth of epidermis.

The herbal preparation, based on the herbal extract from *melittis* (*Melittis melissophyllum* L.), contains various active substances such as tannins, polyphenols, flavonoids, amine compounds, bitter substances and mineral salts. All components of the herbal extract, with their percentage content in the entire extract, are listed in a table below. The percentage content of each component was determined by application of gas chromatography method with mass spectrometry (GC-MS).

| Compound | RI$^{eks.}$ | RI$^{lit.}$ | Content (%) |
|---|---|---|---|
| Ethylene glycol, di-TMS | 992 | 994 | 0.04 |
| Lactic acid, di-TMS | 1071 | 1073 | 0.09 |
| Glycolic acid, di-TMS | 1086 | 1083 | 0.04 |
| 3-Hydroxypropionic acid, di-TMS | 1154 | — | 0.05 |
| Glycerol, tri-TMS | 1294 | 1292 | 4.42 |
| Benzeneacetic acid, TMS | 1299 | 1299 | 0.03 |
| Succinic acid, di-TMS | 1324 | 1324 | 0.54 |
| Glyceric acid, tri-TMS | 1351 | 1348 | 0.07 |
| 3,4-Dihydrocoumarin | 1377 | 1378 | 0.07 |
| Hydroquinone, di-TMS | 1408 | 1410 | 0.05 |
| Coumarin | 1431 | 1432 | 3.01 |
| Malic acid, tri-TMS | 1511 | 1512 | 0.19 |
| Cinnamic acid, TMS | 1544 | 1549 | 0.04 |
| Tyrosol, di-TMS | 1578 | 1582 | 0.10 |
| 2-Hydroxyphenylpropanoic acid, di-TMS | 1690 | — | 3.15 |
| Vanillic acid, di-TMS | 1775 | 1776 | 0.03 |
| Azelaic acid, di-TMS | 1808 | 1808 | 0.10 |
| o-Coumaric acid, di-TMS | 1815 | 1811 | 1.54 |
| Protocatechuic acid, tri-TMS | 1836 | 1837 | 0.05 |
| Quinic acid, penta-TMS | 1901 | 1901 | 2.48 |
| Phytol, TMS | 2183 | 2187 | 1.02 |
| Campesterol, TMS | 3253 | 3251 | 0.13 |
| Stigmasterol, TMS | 3284 | 3285 | 0.33 |
| β-Sitosterol, TMS | 3341 | 3345 | 0.78 |
| Carbohydrates, among others: | | | 57.19 |
| α-Fructofuranose, penta-TMS | 1846 | 1843 | 2.80 |
| β-Fructofuranose, penta-TMS | 1855 | 1854 | 8.93 |
| α-Glucopyranose, penta-TMS | 1933 | 1932 | 7.64 |
| β-Glucopyranose, penta-TMS | 2032 | 2032 | 7.44 |
| Saccharose, octa-TMS | 2715 | 2714 | 8.81 |
| Fatty acids, among others: | | | 18.03 |
| Palmitic acid, TMS | 2052 | 2052 | 5.13 |
| Linoleic acid, TMS | 2214 | 2215 | 1.69 |
| Linolenic acid, TMS | 2223 | 2218 | 9.95 |
| Amino acids | | | 0.19 |
| Resin acids | | | 1.47 |
| Other compounds | | | 4.77 |

RI eks.—Extract retention index, and for comparison with the database
RI lit.—Extract retention index from literature.
Content (%) total record of the % share of compounds (calculated from the chromatogram for individual files)

The studies on the herbal preparation showed the highest amounts of tannins in the herbal preparation having astringent properties and ability to create, especially with collagen, insoluble and irreversible connections which are not subject to putrefaction.

Moreover, tannins act astringently on mucous membranes, inhibit their permeability, preventing microbleeds from blood capillaries. The tannins also inactivate bacteria and their toxins, and have anti-inflammatory properties. Therefore, the *melittis* extract can be successfully used to accelerate treatment of herpes simplex.

In addition, according to the present patent application, flavonoids as a means of sealing walls of small blood vessels have been used as an anti-bleeding substance, preventing ecchymosis and varicose veins. Their activity is associated with inhibition of enzymes present in vessel walls—hyaluronidase, which is responsible for degradation of one of the intracellular substances and increase permeability of spaces between cells. It have also been established that flavonoids have an anti-aggregation effect on platelets.

In addition to the compounds mentioned above, the extract of gingerbread also contains a number of hydroxyl acids, which are used in treatment of acne. Acne is one of the most common dermatoses occurring during puberty. One of the etiopathogenic factors of acne is the excessive development of microflora on the surface of the skin. The most important bacteria responsible for formation of skin lesions is *Propionibacterium acnes*, a Gram-positive anaerobic bacteria. The hydroxyl acids contained in the extract show exfoliative and antibacterial properties that can be used to treat acne lesions.

Inclusion of *Melittis melissophyllum* L. to cultivation resulted in obtaining, on the one hand, a standardized raw material with specified quality parameters, and on the other hand, an increase of population of this plant in its natural environment, thus reducing risk of its extinction.

DETAILED DESCRIPTION

The present patent application contains examples. The examples should not, however, be perceived as any kind of limitation since they are only provided as an illustration of application of the herbal preparation.

According to the present application the herbal preparation, containing an extract from *Melittis melissophyllum* L., is used to treat wounds of an epidermis and deeper layers of skin where inflammatory processes have occurred.

EXAMPLE I

A following semi-solid preparation was prepared for the study which was obtained by mixing together:
- 40% w/w *Melittis melissophyllum* L. from the whole plant,
- 20% w/w of 96% ethyl alcohol,
- 40% w/w Vaseline album—a hydrocarbon based substance used in lipophilic ointments.

The substance, etched by ethyl alcohol, is dissolved with help of heat in a smooth ointment medium for better dispersion of biologically active substances contained in the test extract. It could also be mixed in a cold lipophilic medium. It is important that the substance has been dissolved in the medium at the concentration below saturation.

In the study three groups of mammals with open wounds were involved:

I control group—no treatment was applied to the wound, even antiseptic one.

II group—a typical antiseptic agent was used, chlorhexidine, in accordance with a standard protocol regarding a treatment of an infected wound.

III group—the herbal preparation with a *Melittis melissophyllum* L. extract was used.

Phagocytic activity of white blood cells was assessed using phagocytic index (PI)—a percentage of phagocytes containing absorbed latex particles, and an amount of phagocytes (IF)—the average number of particles per phagocyte.

Tests results of an impact of application of the alcoholic extract of *Melittis melissophyllum* L. during epithelialization (epidermal) and the wound healing in mammals are showed in Table 1.

Test results determining a level of phagocytic activity of leukocytes in healing of the wound surface after application of the alcoholic extract of *Melittis melissophyllum* L. in mammals are showed in Table 2.

TABLE 1

| | Group | | |
|---|---|---|---|
| | Control | Chlorhexidine | *Melittis melissofillum* L. |
| Beginning epitelialization, 24-hours | 5.0 ± 0.4 | 3.9 ± 0.4 | 3.5 ± 0.2 |
| Beginning of rejection of the crust, 24-hours | 9.0 ± 0.5 | 7.6 ± 0.5 | 6.5 ± 0.4 |
| Full crust rejection, 24-hours | 11.5 ± 0.3 | 10.5 ± 0.3 | 7.8 ± 0.5 |
| Complete wound healing, 24-hours | 13.00 ± 0.91 | 11.25 ± 0.19 | 9.3 ± 0.7 |

TABLE 2

| | Time after granulation | | | | | |
|---|---|---|---|---|---|---|
| | 3 day | | 5 day | | 7 day | |
| Group | PI, % | IF | PI, % | IF | PI, % | IF |
| Control | 54.60 ± 1.12 | 7.0 ± 1.2 | 82.00 ± 2.28 | 11.0 ± 2.5 | 66.20 ± 4.16 | 12.5 ± 3.0 |
| Chlorhexidine | 61.60 ± 9.49 | 10.0 ± 2.5 | 59.01 ± 4.58 | 14.0 ± 3.0 | 48.20 ± 5.51 | 11.0 ± 3.0 |
| *Melittismelissofillum* L. | 82.40 ± 1.40 | 16.0 ± 3.5 | 89.00 ± 0.45 | 22.0 ± 2.8 | 41.20 ± 3.50$^a$ | 9.0 ± 1.5 |

PI = FI – phagocytic index – the percentage of phagocytes containing latex particles.
IF = FF – the amount of phagocytes – the average number of particles per 1 phagocyte.

It was established during the tests that the extract from *Melittis melissophyllum* L. accelerates the wounds healing in the experimental group of mammals as compared to the wounds healing in the control group. The first regional crust rejection in the third group started in 6-7 days. In the control groups, in saline or chlorhexidine, in 9 and 7-8 days, respectively. The final crust rejection in the third group took place in 7-8 days. In the control group in 10-11 days. Animals receiving the herbal extract from *Melittis melissophyllum* L. had complete epithelialization of the wound surface on the 9-th day, while in the control group, having saline solution or chlorhexidine applied to the wound surface, a full epithelialization of the wound surface was observed on the 12-th or 13-th day.

The established phagocytic activity of neutrophil white blood cells from the wound surface in different periods of the wound healing, i.e. an increase in phagocytic index and number of phagocytes due to presence of the *Melittis melissophyllum* L. extract, is shown in Table 2. It was found for the first time that the *Melittis melissophyllum* L. extract has a high therapeutic activity during a wound healing period in all stages of the wound healing, accelerating the wound repair process and cells proliferation, therefore ensuring the complete wound healing much earlier.

Mechanisms of action of the *Melittis melissophyllum* L. extract are apparently caused by vasodilation and normalization of microcirculation disorders, improved metabolism of tissues, increased amount and phagocytic activity of neutrophils from the surface of the healing wounds and skin, and macrophage activation, directly or indirectly affecting proliferation of fibroblasts and angiogenesis.

EXAMPLE II

A following herbal preparation was prepared for the study consisted of:
- 40% w/w of the alcoholic extract of *Melittis melissophyllum* L. obtained from the whole plant and etching of dry raw a material by 96% ethyl alcohol,
- 20% w/w of 96% ethyl alcohol,
- glycerol in the amount of 2% w/w, triethylamine in the amount of 2% w/w,
hydroxycellulose in the amount of 1% w/w,
purified water (*aqua purificata*) in the amount of 35% w/w.

The herbal preparation applied in a treatment of open wounds. It was used in a similar way as described in Example I. The experiment confirmed that the herbal preparation based on *Melittis melissophyllum* L. definitely accelerates repair processes during the wound healing. The complete wound healing was accomplished significantly faster than when applying typical antiseptic agents.

EXAMPLE III

A following herbal semi-sold preparation was prepared for the study consisted of:
40% w/w *Melittis melissophyllum* L. from the whole plant,
20% w/w of 96% ethyl alcohol,
40% w/w Vaseline album—a hydrocarbon based substance used in lipophilic ointments.

The herbal preparation applied in a treatment of herpes simplex in human. The preparation was used by men in age 40-45 from the second day after the onset of the herpes symptom. The complete healing was accomplished significantly faster (treatment time has been reduced from 14 to 7 days) than when applying typical antiseptic agents and commonly known and used herbal preparations for the treatment of herpes.

The invention claimed is:

1. A herbal preparation for treatment of herpes and acne comprising:
a plant extract emulsified or suspended in an organic based medium containing, as an active substance, an alcoholic extract from *Melittis melissophyllum L.*, and other active substances including flavonoids in the amount of from 3.6% to 13.4% by weight, polyphenols in the amount of from 11.25% to 45% by weight, tannins in the amount of from 5% to 8% by weight, amine compounds in the amount of from 0.475% to 1.9% by weight, bitter substances in the amount of from 11.55% to 46.2% by weight, and mineral salts in the amount of from 6% to 10% by weight.

2. The herbal preparation according to claim 1 characterized in that the alcoholic extract of melittis contains a *Melittis melissophyllum L.* herb in the amount from 10% to 40% w/w, and ethyl alcohol in the amount from 10% to 20% w/w.

3. The herbal preparation according to claim 2 characterized in that it contains as an organic petroleum jelly album in the amount from 40% to 70% w/w.

4. The herbal preparation according to claim 2 characterized in that it contains as an organic basis comprising glycerol or propylene glycol in the amount of 2% w/w, trimethylamine in the amount of 2% w/w, hydroxycellulose in the amount of 1% w/w, and purified water, *aqua purificata*, in the amount from 30 to 35% w/w.

5. The herbal preparation according to claim 1, wherein the herbal preparation is applied to wounds, skin inflammations or chronic and inflammatory complications after a surgery, thereby increasing an amount and phagocytic activity of neutrophils from the surface of healing wounds and skin.

6. The herbal preparation according to claim 1 characterized in that it leads to a normal growth of epithelium and epidermis, accelerates granulation of skin tissues, maintains moisture of wound environment, and to self-cleaning of the skin inflammations and occurrences of herpes and acne.

7. The herbal preparation according to claim 1 characterized in that it comprises the highest amounts of tannins with astringent properties and ability to create, with collagen, insoluble and irreversible connections that are not subject to putrefaction.

8. The herbal preparation according to claim 7 characterized in that the tannins act astringently on mucous membranes, inhibit their permeability-prevent microbleeds from blood capillaries, inactivate bacteria and their toxins, and have anti-inflammatory properties.

9. The herbal preparation according to claim 1, further comprising an extract of gingerbread contains a number of hydroxy acids which are used in treatment of acne caused by excessive development of microflora on a surface of a skin, wherein the hydroxy acids contained in the extract have exfoliative and antibacterial properties that are used to treat acne lesions.

10. A herbal preparation comprising a mixture of 40% w/w of an alcoholic extract from *Melitti smelissophyllum L.* obtained from extracting a whole dry raw plant material by 96% ethyl alcohol, 20% w/w of 96% ethyl alcohol, glycerol in the amount of 2% w/w, triethylamine in the amount of 2% w/w, hydroxycellulose in the amount of 1% w/w, and purified water, *aqua purificata*, in the amount of 35% w/w, used for an accelerated treatment of wounds and skin inflammations, herpes and acne without causing side effects.

11. The herbal preparation according to claim 10 wherein presence of *Melittis melissophyllum L.* accelerates repair processes of tissues during a treatment of the wounds and skin inflammations, herpes and acne.

\* \* \* \* \*